United States Patent [19]

Radatus et al.

[11] Patent Number: 5,519,129
[45] Date of Patent: May 21, 1996

[54] COMPLEX OF GUANIDINE AND AZT

[75] Inventors: Bruno K. Radatus; Khashayar Karimian, both of Brantford, Canada

[73] Assignee: ACIC (Canada) Inc., Ontario, Canada

[21] Appl. No.: 326,854

[22] Filed: Oct. 21, 1994

Related U.S. Application Data

[63] Continuation of Ser. No. 914,104, Jul. 16, 1992, Pat. No. 5,387,677, which is a continuation of Ser. No. 717,831, Jun. 21, 1991, abandoned.

[51] Int. Cl.[6] ........................ C07H 19/073; C07C 279/02
[52] U.S. Cl. .......................... 536/28.54; 564/230
[58] Field of Search ................... 536/55.3, 28.54; 564/230

[56] References Cited

U.S. PATENT DOCUMENTS

| | | | |
|---|---|---|---|
| 4,211,773 | 7/1980 | Lopez et al. | 514/49 |
| 4,724,232 | 2/1988 | Rideout et al. | 514/50 |
| 4,818,538 | 4/1989 | Rideout et al. | 514/50 |
| 4,818,750 | 4/1989 | Rideout et al. | 514/50 |
| 4,828,838 | 5/1989 | Rideout et al. | 514/50 |
| 4,833,130 | 5/1989 | Rideout et al. | 514/50 |
| 4,837,208 | 6/1989 | Rideout et al. | 514/50 |
| 4,837,311 | 6/1989 | Tam et al. | 536/27.14 |
| 4,847,244 | 7/1989 | Rideout et al. | 514/50 |
| 4,857,511 | 8/1989 | Rideout et al. | 514/50 |
| 4,874,609 | 10/1989 | Rideout et al. | 514/50 |
| 4,874,751 | 10/1989 | Beachman, III et al. | 514/50 |
| 4,904,770 | 2/1990 | Starrett, Jr. et al. | 536/27.14 |
| 4,916,218 | 4/1990 | Almond et al. | 536/28.54 |
| 4,917,900 | 4/1990 | Jones et al. | 424/493 |
| 4,921,950 | 5/1990 | Wilson | 536/28.54 |

FOREIGN PATENT DOCUMENTS 0217580  4/1987  European Pat. Off. .

OTHER PUBLICATIONS

Patthy et al. J. Biol. Chem. 250(2): 557–564, 1975.

*Primary Examiner*—Douglas W. Robinson
*Assistant Examiner*—Gary L. Kunz
*Attorney, Agent, or Firm*—Nixon & Vanderhye

[57] ABSTRACT

A composition of a 1:1 molar complex of guanidine and 3'-azido-3'-deoxythymidine (AZT) which is generated at about pH above 9 and disrupted by pH below about 9. This complex is a useful intermediate in the purification of AZT.

12 Claims, No Drawings

COMPLEX OF GUANIDINE AND AZT

CROSS-REFERENCE TO RELATED APPLICATION

This is a Rule 60 continuation of application Ser. No. 07/914,104, filed 16 Jul. 1992, now U.S. Pat. No. 5,387,677, which is a continuation in part of U.S. Ser. No. 07/717,831, filed 21 Jun. 1991, now abandoned.

BACKGROUND OF THE INVENTION

1. Field of the Invention

The present invention relates to a process for recovering nucleoside derivatives. More particularly, the present invention relates to a process for recovering 3'-azido-3'-deoxythymidine or derivatives thereof directly from the reaction mixture and from the mother liquor remaining from a general process for production thereof.

2. Brief Description of the Prior Art

Nucleoside derivatives having anti-viral activity are known. For example, U.S. Pat. No. 4,211,773 (Lopez et al) discloses pyrimidine nucleosides, specifically, 5-substituted-1-(2'-deoxy-2'-substituted-β-D-arabinofuranosyl) pyrimidine nucleosides which exhibit anti-viral effects. These compounds have the following general formula:

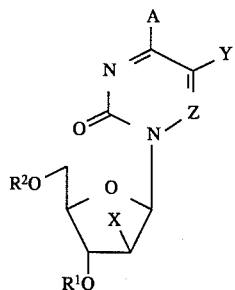

wherein A may be, inter alia, an oxyalkyl group; B may be oxygen or sulfur; X may be, inter alia, a halogen; Y may be, inter alia, a halogen or a substituted or non-substituted amino group; Z may be methyne or nitrogen; and each of $R^1$ and $R^2$ may be, inter alia, hydrogen.

Further, as disclosed in U.S. Pat. No. 4,904,770, other thymidine derivatives have been reported to possess in vitro activity specifically against the AIDS virus. The compound 2',3'-dideoxy-2',3-didehydrothymidine (d4T) is such a thymidine derivative and has the following general formula:

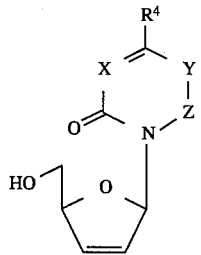

wherein each of X, Y and Z may be, inter alia, nitrogen or C-H and $R^4$ may be OH or $NH_2$.

3'-Azido-3'-deoxythymidine, also known commercially as AZT or zidovudine, is one of the most commonly known nucleoside derivatives having activity against the AIDS virus and thus, is useful in treating humans infected with the virus. Pharmaceutically basic salts of AZT as well as 5'-mono-, di- and tri-phosphates of AZT or basic salts thereof (i.e. derivatives thereof) are also useful in treating AIDS. As is well known in the art, zidovudine has the following chemical formula:

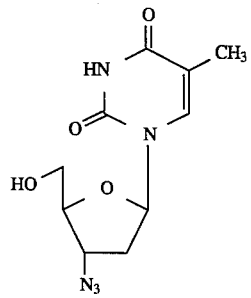

Various methods of producing and/or using zidovudine or related compounds such as the pharmaceutically basic salt thereof and the 5'-mono-, di- or tri- phosphate thereof are disclosed in *J. Org. Chem.* 38, 4299 (1973) (Glinski et al), *Nucleosides and Nucleotides*, 9, 629 (1990) (Watanabe et al), and in U.S. Pat. No. 4,724,232 (Rideout et al), U.S. Pat. No. 4,818,538 (Rideout et al), U.S. Pat. No. 4,818,750 (Rideout et al), U.S. Pat. No. 4,828,838 (Rideout et al), U.S. Pat. No. 4,833,130 (Rideout et al), U.S. Pat. No. 4,837,208 (Rideout et al), U.S. Pat. No. 4,847,244 (Rideout et al), U.S. Pat. No. 4,857,511 (Rideout et al), U.S. Pat. No. 4,874,609 (Rideout et al), U.S. Pat. No. 4,916,218 (Almond et at), the contents of each of which are hereby incorporated by reference.

Large scale manufacture of zidovudine based on one or more of the methods of production referred in the previous paragraph is known. The resultant crude crystalline zidovudine can be recrystallized to pharmaceutically acceptable purity (i.e. purity greater than 99.5%) by conventional techniques. Unfortunately, while these techniques may be useful to reduce the levels of impurities, they require multiple recrystallization steps and thus the efficiency of the recovery of pharmaceutical grade zidovudine is significantly less than theoretical, typically from about 30 to about 60 percent at most. For example, Glinski et al (see above) report a yield of only about 30 percent of theoretical. Since the cost of producing zidovudine can easily exceed US$5000/kg, any yield of the final product (e.g. in pharmaceutically pure form) significantly less than theoretical is indicative of a relatively inefficient process. In light of this, it would be desirable to have an improved process for recovery of zidovudine or derivatives which results in an overall improved yield of the final product.

SUMMARY OF THE INVENTION

It is an object of the present invention to provide a novel process for the recovery of zidovudine or derivatives thereof from a mixture comprising, inter alia, zidovudine or derivatives thereof.

Novel anti-viral compounds as disclosed having the following general formula:

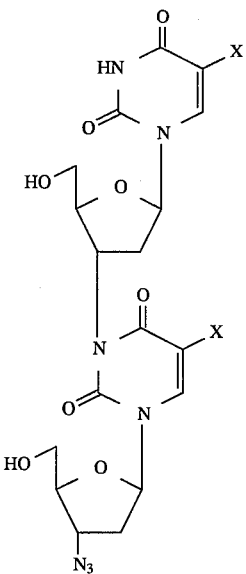

wherein X is selected from the group comprising hydrogen, methyl, trifluoromethyl, propenyl, fluoro, chloro, bromo and iodo.

In the development of these "dimer" anti-viral compounds, a process has been discovered whereby it is possible to produce enhanced yields of zidovudine or derivatives thereof. The process disclosed for production of the "dimer" anti-viral compounds comprises the coupling reaction of a pyrimidine derivative and a 3'-azido-3'-deoxy-5'-o-substituted-pyrimidine compound. A preferred example of the latter compound is zidovudine. It has now been discovered that, in cases where the production of zidovudine forms a part of an overall process for producing the "dimer" anti-vital compound, substantial prevention of co-crystallization of the "dimer" anti-viral compounds can actually lead to enhanced yields of zidovudine. This offers a degree of control in the use of the present invention. Specifically, one can substantially prevent co-crystallization of the "dimer" anti-viral compounds which can lead to an enhanced yield of zidovudine and the increased percentage of the dimer in the mother liquor from the reaction may be recovered by any suitable means such as chromatographic techniques.

Accordingly, this aspect of the present invention provides a process for recovering zidovudine or a derivative thereof from a mixture of chemicals comprising zidovudine or a derivative thereof, the process comprising the steps of (i) reacting zidovudine or a derivative thereof in the mixture with a reagent selected from the group consisting of guanidine, a combination of a base and a guanidine salt, and mixtures thereof, to precipitate a salt;

(ii) acidifying the precipitated salt to a pH of less than about 9 to produce substantially pure zidovudine or a derivative thereof; and (iii) recovering the substantially pure zidovudine or a derivative thereof.

By using this process, the co-crystallization of the "dimer" anti-viral compounds is substantially minimized and results in enhanced yields of substantially pure zidovudine or a derivative thereof.

The choice of guanidine salt is not particularly restricted and guanidine salts are generally known to those skilled in the art. Non-limiting examples of suitable guanidine salts include chloride, bromide, iodide, sulfate, phosphate, acetate, nitrate and carbonate. The preferred guanidine salt is chloride.

The term "base", as used herein with reference to Step (i), includes any compound which is capable of acting as a Lewis base (i.e. a substance that can donate a pair of electrons to the formation of a covalent bond). Suitable bases may be selected from the group consisting of alkali metal compounds, alkali earth metal compounds, ammonium hydroxide and organic base compounds. Non-limiting specific examples of alkali metal compounds include: lithium hydroxide, potassium hydroxide, and preferably sodium hydroxide. Non-limiting examples of alkali earth metal compounds include: magnesium oxide, magnesium hydroxide, calcium oxide, barium oxide, barium hydroxide, and most preferably calcium hydroxide. Non-limiting examples of organic base compounds include alkyl amines such as $R^1R^2R^3N$ wherein $R^1, R^2$ and $R^3$ may be the same or different and are selected from the group comprising $C_{1-10}$ alkyl groups and hydrogen. Preferred examples include methylamine, ethylamine, isopropylamine, n-butylamine, tert-butylamine, dimethylamine, diethylamine, diisopropylamine, triethylamine, piperidine and piperazine. Preferred organic bases include isopropylamine, n-butylamine, tert-butylamine, diethylamine, diisopropylamine and triethylamine.

DETAILED DESCRIPTION OF THE INVENTION

The present process is-useful in the recovery of zidovudine or a derivative thereof from a mixture of chemicals comprising zidovudine or a derivative thereof (hereinafter referred to as "the zidovudine recovery process"). As used throughout the present specification, the terms "recovery" or "recovering" in the context of zidovudine or a derivative thereof are intended to mean that substantially pure zidovudine or a derivative thereof are reclaimed from a source of substantially impure zidovudine or a derivative thereof. The term "pure zidovudine or a derivative thereof" is intended to mean that the zidovudine or derivative thereof is sufficiently pure to be considered by those skilled in the art to be pharmaceutical grade, i.e. at least about 99.5% pure. By analogy, the term "impure zidovudine or a derivative thereof" is intended to mean that the zidovudine or derivative thereof is not sufficiently pure to be considered by those skilled in the art to be of pharmaceutical grade, i.e. less than about 99.5% pure.

The mixture of chemicals comprising zidovudine or a derivative thereof may be considered a source of impure zidovudine or a derivative thereof. Generally, the exact source of this mixture of chemicals is not restricted. For example, the mixture may evolve from a conventional process for the production of zidovudine such as that disclosed by *J. Org. Chem.* 38, 4299 (1973) (Glinski et al) and *Nucleosides and Nucleotides*, 9, 629 (1990) (Watanabe et al). In such a case, the present process may be used as a purification or isolation step in an overall process for the production of zidovudine or a derivative thereof. Alternatively, the present process may be utilized advantageously to reclaim zidovudine or a derivative thereof from the mother liquor of the purification step of the conventional process discussed above. In either of these embodiments, the overall yield of substantially pure zidovudine or a derivative thereof which may be obtained using the present process may be as high as 75% or more for the two steps. This can translate into significant overall savings on the cost of conducting the overall process.

The term "derivative" as used herein in the context of a derivative of zidovudine is intended to cover compounds such as pharmaceutically acceptable salts of zidovudine. Non-limiting examples of such salts alkali metal salts (e.g. sodium, potassium, etc.), alkaline earth salts, organic bases (e.g. amines, etc.) and ammonium salts. Other derivatives of zidovudine which are useful in the present process include the mono-, di- and triphosphates of zidovudine whose chemical formulae are, respectively:

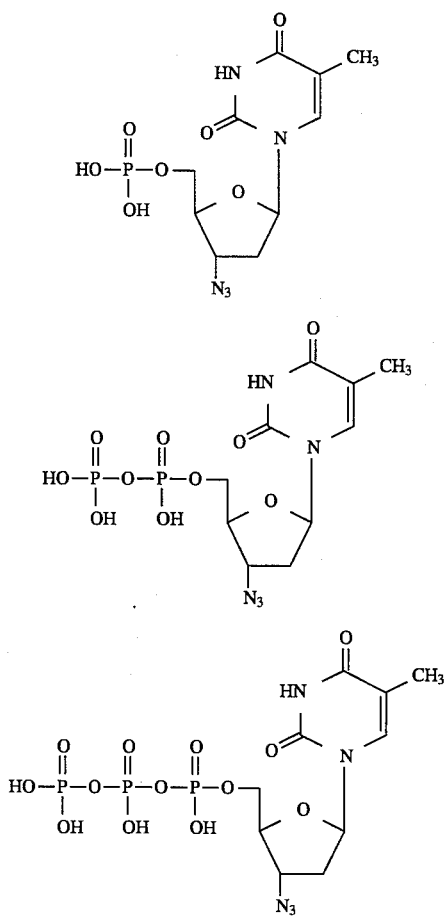

In Step (i) of the present process, zidovudine or a derivative thereof may be reacted with guanidine to form a precipitated salt. Alternatively, and preferably, zidovudine or a derivative thereof is reacted with a combination of a base and a guanidine salt (preferably guanidine chloride) to form a precipitated salt.

In either case, the so-formed salt precipitates from most aqueous and non-aqueous solvents. Accordingly, the choice of solvent for use in Step (i) of the present process is not particularly restricted. Preferably, the solvent is polar, more preferably the solvent is selected from the group consisting of water, alcohols (e.g. methanol, ethanol and isopropanol) and ketones (e.g. methylisobutyl ketone and acetone). Most preferably, the solvent is water.

The manner in which zidovudine or a derivative thereof is reacted with guanidine in Step (i) of the present process is not particularly restricted. In one embodiment, zidovudine may be dissolved in a suitable solvent such as ethanol, to which is added an ethanolic solution of guanidine. In this embodiment, the ethanolic solution of guanidine may be derived by suspending guanidine hydrochloride in ethanol, adding sodium hydroxide (e.g. 50%) or any other suitable base and filtering off the precipitated sodium chloride. Alternatively, in a second embodiment, zidovudine may be suspended in water and solubilized by addition of sodium hydroxide (e.g. 50%) or any other suitable base until a pH of from about 12 to about 13 is reached. In this embodiment the concentration of the base used is not particularly critical provided at least about 1.0, more preferably from about 1.0 to about 1.1, molar equivalents of base are added. This generally results in a pH of the overall mixture in the range of from about 10 to about 14, preferably from about 12 to about 13. Thereafter, guanidine hydrochloride may be added to the zidovudine solution as a solid or as an aqueous solution.

Step (ii) in the present process comprises acidifying the precipitated salt produced in Step (i) to produce substantially pure zidovudine or a derivative thereof. The choice of acid is not particularly restricted provided that it is capable of adjusting the pH of the mixture to less than about 9, preferably in the range of from about 1 to about 9, more preferably in the range of from about 6 to about 8, most preferably about 7. Preferably, acidification is done in an aqueous solvent, more preferably water. Non-limiting examples of acids suitable for use in Step (ii) include the hydrohalogens (chloride, bromide, iodide), acetic, sulfonic, sodium hydrogen sulfate, phosphoric, and monosodium phosphate acids. Preferred acids are hydrochloric acid, acetic and sulfonic acid. The most preferred acid is acetic acid.

In one embodiment of Step (ii), a volume of water equivalent to the weight of the salt produced is mixed with one equivalent of hydrochloric acid (e.g. 32% w/w) and heated to a temperature in the range of from about 75° to about 80° C. The salt is then added to and dissolved in this hot solution after which the pH of the solution is further adjusted, if necessary, to less than about 9, preferably in the range of from about 1 to about 9, more preferably in the range of from about 6 to about 8, most preferably about 7, by further addition of hydrochloric acid (e.g. 32% w/w) or any other suitable acid. More preferably, 1 equivalent of acetic acid is used at 70° C. to 95° C., giving a pH of approximately 6–7, and upon cooling crystallization will occur. Acetic acid permits the use of stainless steel reactors. Crystallization may be induced by cooling the pH-adjusted solution by about 5° C. During cooling, if crystals do not readily form, it is preferred to seed the solution at 45° C. As is known in the art of crystallization, seeding involves addition of a small amount of pure crystals of the compound to be reclaimed to a solution of the compound. Crystals of the compound then "grow" on the added seed.

The crystals of zidovudine or a derivative thereof may then be recrystallized in a conventional manner to yield substantially pure zidovudine or a derivative thereof. In Step (iii) of the present process, the relatively pure zidovudine or a derivative thereof may be recovered by an conventional physical separation technique such as filtration, decantation, evaporation and the like. Of course a combination of these techniques may also be used. If the recovered zidovudine is not substantially pure (i.e. purity of at least 99.5%), it may be subjected to further conventional purification techniques.

The mother liquor from crystallization in Step (ii) of the process typically contains a small amount of zidovudine or a derivative thereof. At least a portion of this residual amount may be recovered by adding sodium hydroxide (or any other suitable base) in a 1.0 or less, preferably a 0.5 or less, equivalent amount to the acid (e.g. hydrochloride) used. The resulting precipitate may be recycled to the initial stage of Step (ii) of the process.

The invention will be further described by reference to the following non-limiting specific examples:

EXAMPLE 1

A sample of impure zidovudine (18.76 g: 81.4% zidovudine and 18.6% 3'-N"-(3'"-azido-3"-deoxythymid-3"-yl)-3'-deoxythymidine dimer was dissolved in hot methanol (57 mL). Guanidine hydrochloride (7 g, 0.0733 moles) was dissolved in methanol. It will be appreciated by those skilled in the art that the terms guanidine chloride and guanidine hydrochloride may be used interchangeably and describe the same compound. 50% caustic (5.6 g=0.07 moles) dissolved in methanol (17 mL) was added to the guanidine hydrochloride solution and the mixture was stirred for 30 minutes. After stirring, the mixture was filtered and the filtrate was added to the impure zidovudine solution. Crystals began to form after a few minutes. The mixture was stirred at 5° C. for 3 hours and then filtered, washed and dried to yield 15.56 g of precipitate comprising zidovudine guanidine salt.

Subjecting the precipitate to HPLC revealed that it comprised 93.05% zidovudine and 6.85% dimer. HPLC analysis of the mother liquor of the precipitate revealed that it comprised 59.1% zidovudine and 40.9% dimer. The mother liquor may be neutralized, preabsorbed on silica gel and applied to a silica gel column to obtain the dimer using ethylacetate-hexane (7:3) as the eluting solvent.

EXAMPLE 2

A sample of zidovudine (26.7 g) was suspended in water (119 mL), heated and basified with 50% caustic (8.94 g) to pH 12.5. Then guanidine hydrochloride (11.5 g) dissolved in water (15 mL) was added in one portion. A precipitate formed in a few seconds and the mixture was stirred at 5° C. for 4 hours. The crystals were filtered and washed with water to yield 28.71 g of off-white crystals. Concentration of the mother liquor to about ⅓ a volume yielded another 1.28 g of crystals.

EXAMPLE 3

A mixture of water (90 mL) and 32% hydrochloric acid (31.4 g) was heated at 75° C. Zidovudine-guanidine complex (90 g) from Example 1 was added in portions to the aqueous solution and when the addition was completed the pH was 7.56. Thereafter, the pH was adjusted to 1.0 by further addition of 32% hydrochloric acid. The mixture was cooled and crystals formed spontaneously. After several hours the crystals were filtered to yield 61.64 g of crude zidovudine suitable for final purification. 50% caustic (22 g) was added to the mother liquor and a precipitate formed. After 30 minutes the precipitate was filtered to yield 7.99 g zidovudine-guanidine complex suitable for recycling (i.e. acidification).

EXAMPLE 4

A solution of impure zidovudine was prepared by a conventional process modeled after Glinski et al., supra, using 2,3'-O-anhydro-5-O-tritylthyimidine (0.4 moles, 186.6 g) as a starting material. The composition of the major constituents in the reaction mixture can be found with reference to Composition A in Table 1. The theoretical mass of Composition A is 107 g.

Thereafter, Composition A was crystallized from solution to yield 77.97 g of crude zidovudine—see Composition B in Table 1.

The mother liquor from the recrystallization step was concentrated to yield another 3.25 g of zidovudine crystals—see Composition C in Table 1.

The zidovudine crystals from Compositions B and C were combined and purified using conventional techniques which included treatment with active charcoal to yield 62.93 g (0.235 moles, 58.9%) of pharmaceutical grade zidovudine.

The mother liquor from the production of Compositions B and C and the mother liquor from the production of pharmaceutical grade zidovudine were combined and evaporated to yield a syrup (approx. 34 g)—see Composition D in Table 1—which was then dissolved in ethanol (100 mL). Guanidine hydrochloride (15 g) was dissolved in ethanol (23 mL), 50% sodium hydroxide (11.5 g) was added and the resulting mixture was stirred for 10 minutes. The mixture was filtered and the precipitated sodium chloride was washed with ethanol (25 mL). The ethanolic guanidine and the ethanolic substrate solutions were separately heated to 75° C. and then combined with stirring resulting in the formation of a precipitate after about one minute. The mixture was cooled to 5° C., filtered and washed with ethanol to yield 21.62 g of zidovudine guanidine salt—see Composition E in Table 1. The resulting mother liquor from the production of Composition E was concentrated to about ⅓ of the original volume resulting in a yield of a further 1.23 g of zidovudine guanidine crystals—see Composition F in Table 1. The mother liquor from Composition F was thereafter subjected to HPLC—see Composition G in Table 1.

The zidovudine guanidine salts from each of Compositions E and F were combined and thereafter added to a mixture of water (23 mL) and 32% hydrochloric acid (7.98 g) which had been heated to 85° C. The salts were completely dissolved in a few minutes and the pH of the mixture was 8.2. The pH was then adjusted to pH 1 by further addition of 32% hydrochloric acid the mixture was then cooled to ambient temperature and stirred for 16 hours. Thereafter, the mixture was further cooled to 5° C., stirred for 30 minutes, and filtered and washed with water to yield 15.74 g of substantially purified zidovudine—see Composition H in Table 1. The mother liquor from the production of Composition H was basified to pH 12.35 by addition of 50% sodium hydroxide to yield a precipitate which was filtered and washed with water to yield 2.18 g of zidovudine guanidine salt—see Composition I in Table 1—which was of sufficient purity to be recycled with other batches of zidovudine guanidine salts (i.e. combine with salts from Compositions E and F). The mother liquor was acidified to pH 1 and extracted several times with methyl isobutyl ketone and the combined extract was set aside.

The crude zidovudine (15.74 g) from Composition H was purified by recrystallization from water after a charcoal treatment to yield 12.94 g (0.048 moles, 12%) of pharmaceutical grade zidovudine. Accordingly, the overall yield of pharmaceutical grade zidovudine was 70.9% which was representative of a 12% improvement over the prior art technique for producing zidovudine.

The mother liquor from the purification of Composition H was combined with the combined extract from Composition I and evaporated to about 10.4 g—see Composition J in Table 1. Silica column chromatography using first ethylacetate/hexanes 7:3, then ethyl acetate and finally ethanol yielded fractions of dimer (3'-N"-(3'"-azido-3'"-deoxythymid-3"-yl)-3'-deoxythymidine)) which were crystallized from ethanol in two crops to yield 0.91 g. An NMR spectrum of the dimer (500 MHz-DMSO-$d_6$) yielded the following:

| SHIFT (δ) | ASSIGNMENT |
|---|---|
| 1.78 and 1.84 | 2 × 5, 3 × 3H, 2 × $CH_3$ |
| 2.15 | DDD, 1H, $J2_1'2_2'$=13.9 Hz, $J1'2_1'$=7.3, $J2_1'3'$=11.9, $H-2_1'$ |
| 2.33 | DDD, 1H, $J2_1'''2_2'''$=13.6 $J1'''2_1'''$=6.1, $J2_1'''3'''$=7.0, $H-2_1'''$ |
| 2.43 | DDD, $1H_1$, $J1'''2_2'''$=6.1, $J2_2'''3'''$=5.6, $H-2_2'''$ |
| 2.43 | DDD, 1H, $J1'''2_2'$=7.3, $J2_2'3'$=5.8, $H-2_2'$ |
| 3.49 | DDD, 1H, $J5_1'5_2'$=11.7, $J5_1'5'$-OH=5.0, $J5_1'4'$=5.0, $H-5_1'$ |
| 3.56 | DDD, 1H, $J5_2'5$-OH=5.0, $J5_2'4'$=3, $H-5_2'$ |
| 3.59 | DDD, 1H, $J5_1'''5_2'''$=12.1, $J5_1'''5'''$-OH=5.3, $J5_1'''4'''$=3.9, $H-5_1'''$ |
| 3.67 | DDD, 1H, $J5_2'''5'''$-OH=5.3, $J5_2'''4'''$=3.9, $H-5_2'''$ |
| 3.83 | DT, 1H, $J3'''4'''$=5.5, $H-4'''$ |
| 4.11 | M, 1H, $J3'4'$=3.4, $H-4'$ |
| 4.38 | DT, 1H, $H-3'''$ |
| 4.97 | t, 1H, exchangeable, 5'-OH |
| 5.23 | t, 1H, exchangeable, 5'''-OH |
| 5.57 | DDD, 1H, $H-3'$ |
| 6.14 | t, 1H, $H-1'''$ |
| 6.56 | t, 1H, $H-1'$ |
| 7.78 | S, 2H, 2XH-6 |
| 11.27 | S, 1H, exchangeable, NH |

The NMR assignments were made by comparison with the spectrum for zidovudine and by analysis of a 2-dimensional (COSY) experiment which allowed the assignment of the sugar protons to the appropriate furanose ring.

TABLE 1

| Composition | Content of Major Components (% by weight) | | | |
|---|---|---|---|---|
| | 1 | 2 | 3 | 4 |
| A | 86.6 | 4.6 | 3.0 | 2.3 |
| B | 96.4 | 2.1 | 0.08 | 0.96 |
| C | 95.8 | 1.4 | 0.25 | 1.81 |
| D | 68.7 | 6.5 | 9.5 | 9.0 |
| E | 94.4 | 1.2 | 0.06 | 3.19 |
| F | 91.8 | 1.6 | 1.0 | 3.8 |
| G | 19.65 | 18.2 | 37.63 | 19.3 |
| H | 98.2 | 0.8 | — | 0.2 |
| I | 92.84 | 1.4 | — | 1.6 |
| J | 42.8 | 3.2 | 32.6 | 16.6 |

In Table 1, major components referred are as follows:

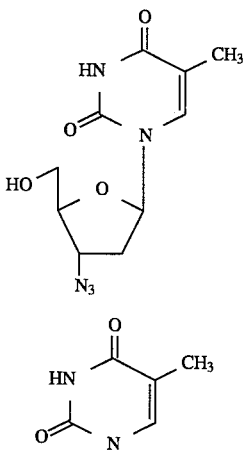

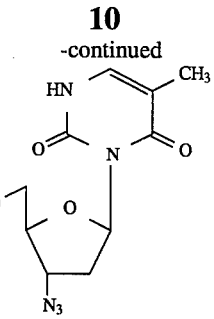

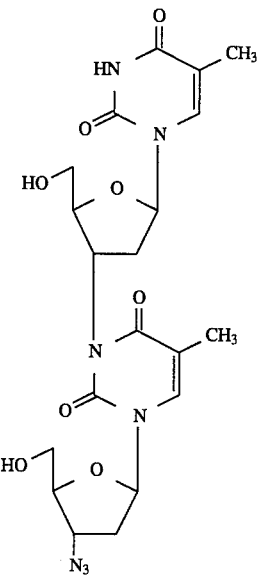

Compound 1: 3'-azido-3'-deoxythymidine (zidovudine)
Compound 2: thymine
Compound 3: 3-(3-azido-2,3-dideoxy-β-D-erythro pentofuranosyl)thymine
Compound 4: 3'-N'''-(3'''-azido-3'''-deoxythymid-3'''-yl)-3'-deoxythymidine

EXAMPLE 5

A basic solution (pH 12.5) of impure zidovudine in water (850 mL) was prepared by a conventional process from 0.8 moles of 2,3'-O-anhydro-5'-O-tritylthymidine. The major constituents in the basic solution are provided as Composition A in Table 2 wherein Compounds 1, 2, 3 and 4 are same as in Table 1 above for Example 6. Guanidine hydrochloride (92 g) was dissolved in water (200 mL) and added to the basic solution. After a few minutes a copious amount of precipitate was formed and the mixture was stirred at ambient temperature for 4 hours. The precipitate was filtered and washed with water to yield 221.19 g of product—see Composition B in Table 2.

The mother liquor from the production of Composition B was concentrated to about ½ the original volume resulting in precipitation of a solid. The solid was filtered and washed to further yield 12.84 g of zidovudine guanidine salt—see Composition C in Table 2. The mother liquor from production of Composition C was acidified to pH 1.0 and extracted several times with methyl isobutyl ketone and the extract was set aside.

A mixture of water (234 mL) and 32% hydrochloric acid (81.7 g) was heated to 85° C. and the combined zidovudine guanidine salt from Compositions B and C was added thereto. Within a few minutes, the salt was dissolved and the pH of the mixture was 6.0. The pH of the mixture was adjusted to 1.0 by addition of 32% hydrochloric acid. Thereafter, the mixture was cooled and stirred for 16 hours. The resultant crude zidovudine was filtered and washed to yield 152.39 g of crystals—see Composition D in Table 2. The mother liquor from production of Composition D was basified to pH 12.75 with 50% sodium hydroxide and stirred for 4 hours. The resultant crystals of crude zidovudine guanidine salt were filtered and washed to yield 22.96 g of product—see Composition E in Table 2—which was recycled as described hereinafter. The mother liquor from production of Composition E was extracted several times with methyl isobutyl ketone and the extracts were set aside.

The crude zidovudine (152.39 g) from Composition D was recrystallized from water by conventional techniques which included a charcoal treatment to yield 135.7 g (0.51 moles, 63.5% ) of pharmaceutical grade zidovudine.

The two methyl isobutyl ketone extracts from treatment of the mother liquors of Compositions C and E were combined and evaporated to a syrup and combined with the mother liquor and further evaporated to 250 mL. The pH of this mixture was adjusted to 12.3 with 50% sodium hydroxide. The mixture was then heated to 70° C. and solid guanidine hydrochloride (16 g) was added and the temperature was increased to 95° C. and then allowed to cool. When the cooling mixture reached 65° C., a precipitate began to form. Cooling was continued to 5° C. when the mixture was filtered to yield 21.99 g of zidovudine guanidine salt—see Composition F in Table 2. The mother liquor from Composition F was acidified to pH 1.0 as above (Compositions C and E), extracted with methyl isobutyl ketone and set aside.

The zidovudine guanidine salt from Compositions E and F were treated in a manner similar to Compositions B and C above to yield 29.44 g crude zidovudine —see Composition G in Table 2. The mother liquor from Composition G was basified to pH 12.2. and the resultant crystals were filtered to yield 4.28 g of zidovudine guanidine salt—see Composition H in Table 2. The mother liquor from Composition H was acidified to pH 1.0 and extracted several times with methyl isobutyl ketone and set aside.

The crude zidovudine (29.44 g) from Composition G was purified to yield 26.7 g (0.1 moles, 12.5%) of pharmaceutical grade zidovudine. Accordingly, the overall yield of pharmaceutical grade zidovudine (162.4 g) was 76% which was representative of a 17.1% improvement over the prior art technique for producing zidovudine.

The mother liquor from the purification step was combined with the mother liquor extracts from Compositions F and H, and evaporated to a syrup, dissolved in ethanol, treated with ethanolic guanidine and the resultant precipitate filtered to yield 3.85 g of crude zidovudine guanidine salt—see Composition I in Table 2. The mother liquor from Composition I was evaporated, the resulting residue was dissolved in water, the pH thereof adjusted to 1.0 and the resulting mixture was extracted several times with methyl isobutyl ketone. The extracts were combined and evaporated to yield 11.39 g of a thin syrup—see Composition J in Table 2. The syrup could be subjected to column chromatography to obtain the dimer (Compound 4), if desired.

An analytical grade sample of the zidovudine guanidine salt was prepared by suspending pharmaceutical grade zidovudine (53.4 g) in water (250 mL) and adding 50% sodium hydroxide (17.6 g) to provide a mixture having a pH of 13.0. The mixture was then heated to 70° C. Thereafter, guanidine hydrochloride (23 g) was added as a solid and the mixture was heated to 97° C. to dissolve the emerging precipitate. The mixture was then set aside to cool and crystallize, and it was stirred for 16 hours. Thereafter, the crystals were filtered and washed with water and ethanol to yield 58.76 (90%) of white crystals. The crystals had a melting point of 210.9°–212° C.

Analytical studies on the guanidine zidovudine salt ($C_{11}H_{18}N_8O_4$) yielded the following results:

|  | C | H | N | O |
|---|---|---|---|---|
| Calculated: | 40.49 | 5.56 | 34.34 | 19.61 |
| Found: | 40.92 | 5.45 | 34.17 |  |

U.V. Spectrum ($H_2O$): $\lambda$ max @268 nm
I.R. Spectrum (KBr disc): 2095 cm$^{-1}$ (indicated of azide bond)
An NMR spectrum of the dimer (500 MH$_2$-DMSO-d$_6$) yielded the following:

| SHIFT ($\delta$) | ASSIGNMENT |
|---|---|
| 1.71 | S, 3H, CH$_3$ |
| 2.12 | m, 1H, H-2$_1$' |
| 2.25 | m, 1H, H-2$_2$' |
| 3.57 | m, 2H, H-5$_1$',-5$_2$' |
| 3.75 | m, 1H, H-4' |
| 4.33 | m, 1H, H-3' |
| 6.12 | t, 1H, H-1' |
| 7.29 | S, 1H, H-6 |
| 7.38 | broad singlet, 7H, exchangeable, 3-NH, 5'-OH, guanidine |

TABLE 2

| Composition | Content of Major Components (% by weight) | | | |
|---|---|---|---|---|
|  | 1 | 2 | 3 | 4 |
| A | 86.6 | 4.6 | 3.0 | 2.3 |
| B | 95.2 | 1.5 | 0.87 | 1.3 |
| C | 92.0 | 2.5 | 1.1 | 1.51 |
| D | 98.26 | 0.68 | — | 0.11 |
| E | 94.7 | 1.4 | 0.12 | 1.6 |
| F | 94.48 | 1.5 | 0.17 | 1.0 |
| G | 97.77 | 0.56 | — | 0.05 |
| H | 93.41 | 1.04 | 0.08 | 2.94 |
| I | 90.58 | 1.63 | 0.57 | 2.97 |
| J | 12.08 | 1.98 | 72.2 | 7.38 |

On this basis, the guanidine zidovudine salt was determined to have the following structure:

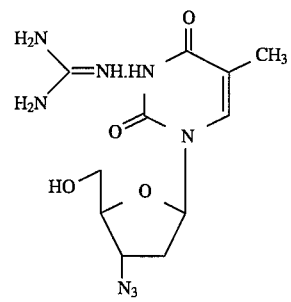

EXAMPLE 6

Zidovudine (3 g) was suspended in water (15 mL) and subjected to mild heat to yield a cloudy mixture. A base (1.2 equivalents)—see Table 3 for nature of base—was added to the mixture and a clear solution resulted. Thereafter guanidine hydrochloride (1.38 g) was added to the solution with stirring. Within a few minutes a precipitate formed (except in the cases of imidazole and pyridine). After one hour, the crystals were filtered, and washed with water and ethanol to yield the guanidine zidovudine salt confirmed by NMR. The exception to this was when the bases were imidazole and pyridine which resulted in the production of the free acid zidovudine (isolated and confirmed by NMR). As is evident from the results in this Example, aromatic heterocyclic amines such as imidazole are not useful in the context of a "base" in Step (i) of the present process.

EXAMPLE 7

A mixture of water (20 mL) and 32% hydrochloric acid—see Table 4 for amount used—was heated to 75° C. and water-damp guanidine zidovudine salt (105 g) having a water content of 38% by weight was added to the mixture. Heating was continued until all material had dissolved. The resultant pH of the solution was measured and then adjusted to a desired pH—see Table 4. The mixture was cooled to 60° C. and seeded. The mixture was further cooled to 25° C. and stirred for 2 hours resulting in the production of crystalline material. The crystals were filtered and washed to yield in all cases approximately the same mount of zidovudine crystals—see Table 4. In each case, the crystals were 99% pure and could be further purified to yield pharmaceutical grade zidovudine (purity of at least 99.5%).

TABLE 3

| Base | Zidovudine Guanidine Salt (g) | % Yield |
| --- | --- | --- |
| Methylamine | 1.87 | 51.0 |
| Isopropylamine | 3.00 | 81.9 |
| n-Butylamine | 2.91 | 74.6 |
| tert-Butylamine | 2.97 | 81.3 |
| Diethylamine | 2.88 | 78.8 |
| Diisopropylamine | 3.10 | 84.6 |
| Piperidine | 2.69 | 73.6 |
| Piperazine | 2.11 | 57.7 |
| Triethyl amine | 2.81 | 76.9 |
| Imidazole | 0.00 | 0.0 |
| Pyridine | 0.00 | 0.0 |

TABLE 4

| Sample | HCl (g) | Resultant pH | Adjusted pH | Zidovudine (g) |
| --- | --- | --- | --- | --- |
| 1 | 20.5 | 1.0 | 1.0 | 40.31 |
| 2 | 18.5 | 7.9 | 5.8 | 40.46 |
| 3 | 18.0 | 8.0 | 8.0 | 38.24 |
| 4 | 18.0 | 8.0 | 6.0 | 39.81 |

The mother liquors from each Sample were basified to pH 12–13 to yield zidovudine guanidine precipitate weighing from 4.5 g to 5.5 g. In each case, the crystals were 91% to 95% pure and could be further recycled to yield substantially pure zidovudinie which in turn could be further purified to yield pharmaceutical grade zidovudine (purity of at least 99.5% ).

EXAMPLE 8

A mixture of water (34 mL) and acetic acid—see Table 5 for amount used—was heated to 75° C. and water-damp guanidine zidovudine salt (105 g) having a water content of 38% by weight was added to the mixture. Heating was continued until all material had dissolved. The resultant pH of the solution was measured and—see Table 5. The mixture was cooled to 60° C. and seeded. The mixture was further cooled to 25° C. and stirred for 2 hours resulting in the production of crystalline material. The crystals were filtered and washed to yield in all cases approximately the same mount of zidovudine crystals—see Table 5. In each case, the crystals were 99% pure and could be further purified to yield pharmaceutical grade zidovudine (purity of at least 99.5%). The NMR of zidovudine isolated when 14.4 g of acetic acid was used showed an acetyl absorption of about 10%. Accordingly, not only is the use of a large excess of acid not required to achieve the same yield of zidovudine, in certain cases, the product may be affected.

TABLE 5

| Sample | Acetic Acid (g) | Resultant pH | Zidovudine (g) |
| --- | --- | --- | --- |
| 1 | 9.6 | 8.2 | 40.95 |
| 2 | 11.0 | 6.5 | 40.73 |
| 3 | 12.0 | 6.0 | 40.26 |
| 4 | 14.4 | 5.5 | 39.39 |

The mother liquors from each Sample were basified to pH 12–13 to yield zidovudine guanidine precipitate weighing from 4.5 g to 6.0 g. In each case, the crystals were 91% to 95% pure and could be further recycled to yield substantially pure zidovudine which in turn could be further purified to yield pharmaceutical grade zidovudine (purity of at least 99.5% ).

We claim:

1. A complex consisting of guanidine and 3'-azido-3'-deoxythymidine (AZT) whose structure is shown below:

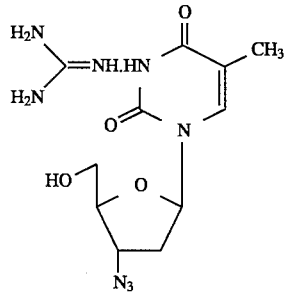

and whose melting point is 210.9° C.–212° C.

2. The complex consisting of guanidine and 3'-azido-3'-deoxythymidine (AZT) prepared by reacting AZT with a reagent selected from the group consisting of guanidine, a combination of a base and guanidine, and mixtures thereof, to form a precipitated complex.

3. The complex of claim 2 wherein the precipitating reagent is a solution of guanidine.

4. The complex of claim 3 wherein the solution of guanidine is prepared by suspending guanidine hydrochloride in a solvent, adding a base thereto to produce a precipitate and filtering said precipitate to provide a filtrate consisting essentially of the solution of guanidine.

5. The complex of claim 4 wherein said base is sodium hydroxide and said precipitate is sodium chloride.

6. The complex of claim 4 wherein said solvent is a polar solvent.

7. The complex of claim 4 wherein said solvent is ethanol.

8. The complex of claim 2 wherein the process for preparing the complex comprises contacting a suspension of AZT with a base to dissolve the AZT yielding a solution having a pH of from about 10 to about 14, and then adding guanidine hydrochloride to the solution.

9. The complex of claim 8 wherein said guanidine hydrochloride is in the form of a solid.

10. The complex of claim 8 wherein said guanidine hydrochloride is in the form of an aqueous solution.

11. The complex of claim 3 wherein said the process is conducted in the presence of a polar solvent.

12. The complex of claim 11 wherein the polar solvent is selected from the group consisting of water, methanol, ethanol, isopropanol, methylisobutylketone, and acetone.

* * * * *